(12) United States Patent
Fiz Sánchez et al.

(10) Patent No.: US 9,642,648 B2
(45) Date of Patent: May 9, 2017

(54) DEVICE FOR ARTHROSCOPIC USE, AND METHOD OF DIAGNOSIS OR TREATMENT OF JOINT AILMENTS USING SAID DEVICE

(71) Applicant: UNIDAD DE CIRUGÍA ARTROSCÓPICA, S.L., Vitoria (Alava) (ES)

(72) Inventors: Nicolás Fiz Sánchez, Vitoria (ES); Mikel Sanchez Álvarez, Vitoria (ES)

(73) Assignee: UNIDAD DE CIRUGÍA ARTROSCÓPICA, S.L., Vitoria (Alava) (ES)

( * ) Notice: Subject to any disclaimer, the term of this patent is extended or adjusted under 35 U.S.C. 154(b) by 380 days.

(21) Appl. No.: 14/222,869

(22) Filed: Mar. 24, 2014

(65) Prior Publication Data

US 2015/0265266 A1    Sep. 24, 2015

(51) Int. Cl.
*A61B 17/56* (2006.01)
*A61B 17/02* (2006.01)
*A61B 17/04* (2006.01)

(52) U.S. Cl.
CPC .............. *A61B 17/56* (2013.01); *A61B 17/02* (2013.01); *A61B 17/025* (2013.01);
(Continued)

(58) Field of Classification Search
CPC ... A61B 17/02; A61B 17/0218; A61B 17/025; A61B 2017/0268; A61B 2017/0275; A61B 17/0281; A61B 17/0401; A61B 2017/0404; A61B 2017/0406; A61B 17/56; A61B 2017/564
See application file for complete search history.

(56) References Cited

U.S. PATENT DOCUMENTS 7,875,057 B2 *   1/2011   Cook ................. A61D 1/00
                                                                128/898
7,892,256 B2 *   2/2011   Grafton ............ A61B 17/06166
                                                                600/37
(Continued)

FOREIGN PATENT DOCUMENTS

FR         2815843 A1 *   5/2002   ......... A61B 17/0401

OTHER PUBLICATIONS

Machine Translation of FR2815843 Retrieved from <http://translationportal.epo.org/emtp/translate/?ACTION=description-retrieval&COUNTRY=FR&ENGINE=google&FORMAT=docdb&KIND=A1&LOCALE=en_EP&NUMBER=2815843&OPS=ops.epo.org/3.1&SRCLANG=fr&TRGLANG=en> on Jun. 15, 2016.*

*Primary Examiner* — Larry E Waggle, Jr.
(74) *Attorney, Agent, or Firm* — Browdy and Neimark, PLLC

(57) ABSTRACT

Method and device used in arthroscopy for the diagnosis or treatment of a joint (2) surrounded at least partially by a capsule (3). The device (1) includes a plate (6) and a traction element (10). The method comprises the steps of inserting the device (1) through the capsule (3) and into the joint (2), allowing the traction element (10) to protrude, and pulling the traction element (10) so that the plate (6) exerts an intra-articular traction of the capsule (3) tissues, creating a space (13) under the plate (6). The formation of this space (13) helps to improve visibility inside the joint (2) without the need for extensive incisions in the capsule (3). Therefore, the capsule (3) is less damaged after the arthroscopy and post-operative complications are minimized for the patient.

7 Claims, 4 Drawing Sheets

(52) U.S. Cl.
CPC ...... *A61B 17/0218* (2013.01); *A61B 17/0281* (2013.01); *A61B 17/0401* (2013.01); *A61B 2017/0268* (2013.01); *A61B 2017/0275* (2013.01); *A61B 2017/0404* (2013.01); *A61B 2017/0406* (2013.01); *A61B 2017/564* (2013.01)

(56) References Cited

U.S. PATENT DOCUMENTS

| | | | | |
|---|---|---|---|---|
| 2007/0162125 A1* | 7/2007 | LeBeau | ............. | A61B 17/0401 623/13.14 |
| 2012/0130492 A1* | 5/2012 | Eggli | ....................... | A61F 2/08 623/13.14 |
| 2012/0316430 A1* | 12/2012 | Aldag | ................... | A61B 17/02 600/424 |

* cited by examiner

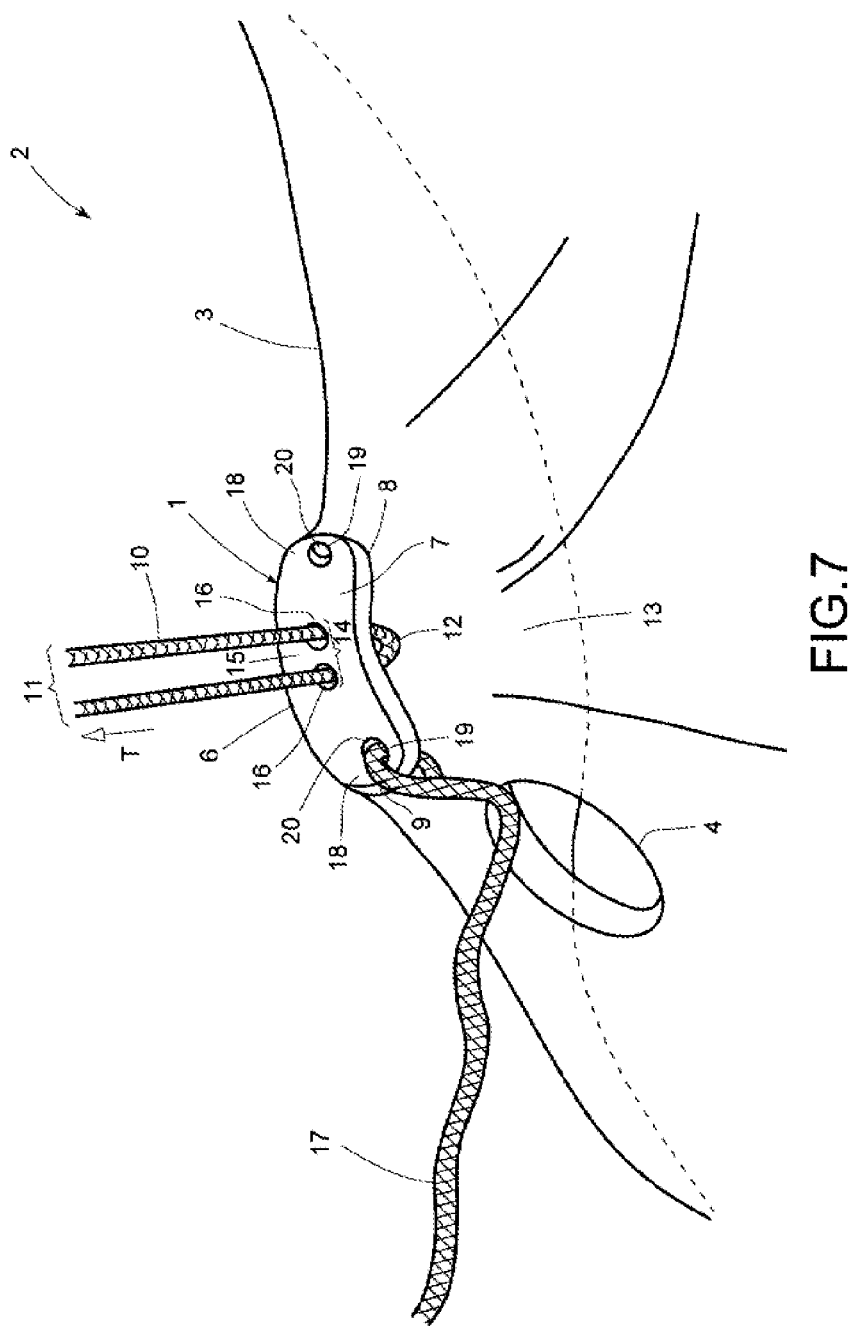

DEVICE FOR ARTHROSCOPIC USE, AND METHOD OF DIAGNOSIS OR TREATMENT OF JOINT AILMENTS USING SAID DEVICE

FIELD OF THE INVENTION

The invention relates to a device suitable for arthroscopic use, and to a surgical method for the diagnosis or treatment of joint ailments using this device.

PRIOR ART

Joints are individual anatomic structures that form points of union between different components of the skeleton such as bones, cartilage and teeth. More specifically, movable joints, also known as synovial or diarthrosis joints, such as the knee, the shoulder or the hip, are points of union between two bones and allow a wide variety of relative mechanical movement between these bones. These movable joints have a resistant capsule around the joint. Due to its resistance, the capsule provides strength and stability to the joint as it strengthens the union between the two bones that make up the joint. A series of ligaments, located around the joint and closely linked to the capsule, strengthen the union between the capsule and the bones that make up the joint and restrict joint movement in certain directions. Thus, the capsule and the associated ligaments make up a functional unit that offers the joint the necessary resistance and stability, whereby movement is possible without excessive or undesired displacement of the bones.

The surgical treatment of joint disorders, injuries or other ailments has been successfully performed recently using arthroscopy. Arthroscopy is a surgical technique that allows access to a joint and the visualization of its internal anatomy without the need for large incisions in the patient's body or the significant or traumatic movement of tissues. Arthroscopy allows for the diagnosis and treatment of a variety of joint pathologies and problems in a minimally invasive process for the patient. A device called an arthroscope, equipped with a light-generating optic system and a small tube or probe with a camera on the end, is used to see inside the joint. The insertion of this camera inside the joint allows the surgeon to see images taken by the camera on a monitor. To insert the camera and other surgical tools into the joint, various small incisions are made (also known as portals). These incisions or portals extend from the skin, through the capsule, and to the joint to be treated. Thanks to the use of these small portals, arthroscopy allows the joint to be treated whilst minimizing tissue damage, with limited associated damage for the patient and, in short, without the need for an invasive surgical operation. Basic arthroscopic techniques include joint biopsies, repair of ligaments and other tissues in the joint, removal of free bodies, and diagnosis and treatment of diverse injuries and pathologies associated with each specific joint. Traditionally, these arthroscopic techniques have been widely used mainly in the knee and shoulder joints as well as in the elbow, wrist or ankle joints.

However, conventional arthroscopy presents certain limitations. On one hand, some joints are difficult to access through conventional arthroscopy. For example, the hip joint does not have an interior cavity that is easy to access and visualize, thus requiring a more specialized technique and a greater skill by the surgeon. On the other hand, as arthroscopy is a technique that does not require large incisions and minimizes the displacement of tissues adjacent to the joint, at times, the presence of these tissues hinders or impedes the proper visualization of the joint. This visibility or exposure of the operating field may be so reduced that it is not possible to carry out the arthroscopy properly. In those cases in which joint visibility is insufficient, it is necessary to make more extensive incisions in the joint tissues in order to obtain appropriate exposure of the operating field: the need for more extensive incisions reduces the advantages of using the arthroscopic technique as it becomes more invasive for the patient.

At present, the common solution to improve joint visibility in hip arthroscopy is to separate, set apart or unbundle the tissues that interfere in the surgeon's field of vision and prevent him/her from working properly. To do so, it is necessary to venture further into the capsule that surrounds the joint through capsulectomies (removal of part of the joint capsule) or capsulotomies (opening the joint capsule). The most commonly used capsulotomies are interportal capsulotomy (incision made between two portals) and T capsulotomy with a cut or additional derivation which is more invasive than the former. Techniques based on the use of capsulotomies or capsulectomies cause injury to the capsule which usually leads to inflammation, pain and other post-operative complications. On the other hand, the importance of keeping the hip joint capsule as intact as possible is well known, due to the capsule's role in the kinetics and stability of the joint. For this reason, once the arthroscopy has been completed, it is necessary to repair or suture the capsule as well as other tissues that may have been damaged. The need to carry out such repairs complicates and extends the duration of the arthroscopy and diminishes the benefits of the arthroscopic technique.

Several recently published works coincide on the importance of the appropriate handling of the capsule during hip arthroscopy. These works also highlight the importance of choosing the best technique in accordance with the specific joint problem to be treated. The aforementioned guidelines are aimed at improving the visibility of the joint without jeopardizing the stability and kinetics of the hip after the operation.

A first example of these works is the publication "Capsular Management During Hip Arthroscopy: From Femoroacetabular Impingement to Instability"; Asheesh Bedi, M.D., Gregory Galano, M.D., Christopher Walsh, M.D. and Bryan T. Kelly, M.D.; Arthroscopy 2011. This publication argues which is the best capsulotomy to treat diverse hip problems; femoroacetabular impingement and joint instability are described as examples of these problems. It also describes in detail how to perform the recommended capsulotomy in each case. The article concludes by indicating potential post-operative complications (with particular reference to heterotopic ossification) derived from an excessive, poorly repaired or inappropriate capsulotomy or capsulectomy.

The problem of these prior art techniques is also described in the publication "Arthroscopic capsulotomy, capsular repair, and capsular plication of the hip: Relation to atraumatic instability"; Benjamin G. Domb, M.D., Brian D. Giordano, M.D., Marc J. Philippon, M.D.; Arthroscopy. 2013. The publication comprehensively reviews the available biomechanical and clinical studies which have shown that the hip joint capsule plays an important role in maintaining the stability of this joint. The article recommends avoiding the indiscriminate practice of capsulotomies. Furthermore, the conclusions of the article point towards an approach aimed at maintaining the integrity of the capsule, through its subsequent repair in order to obtain a higher success rate in the long term.

The objective of the invention is to propose an alternative method of arthroscopy that improves the visibility of the joint during arthroscopy. Furthermore, the invention aims to provide a method that helps to minimize post-operative complications for the patient. The invention also seeks a method that minimizes the aforementioned disadvantages of conventional hip arthroscopy.

BRIEF DESCRIPTION OF THE INVENTION

The object of the invention is a method for the diagnosis or treatment of a patient's joint, whereby this joint is surrounded, at least partially, by a capsule. The method as per the invention comprises a first step consisting in being provided with at least one device fitted with a plate and a traction element; the plate has a first external surface and a second external surface, opposite to each other, and a contour between both external surfaces, whereby this contour is devoid of sharp edges; the traction element protrudes from the first external surface of the plate, forming a variable angle with this first external surface. The method further includes the steps of: inserting the device through the capsule and into the joint, whereby the traction element protrudes externally and is accessible from outside the patient's body; pulling the traction element, so that this traction element is placed in a non-tangent position to the first external surface of the plate, causing the external surface to come into contact with the inside wall of the capsule; and continue pulling the traction element in a non-tangent T direction to the first external surface, making the plate push the internal wall of the capsule and cause a deformation of the capsule, there being formed a space under the plate and inside the joint as a result of this deformation.

By pulling the traction element, the device used in the method according to the invention allows for intra-articular traction of the capsule tissues and other tissues adjacent to the joint. Intra-articular traction should be understood as the traction exercised from inside the joint. Therefore, the device as per the invention enables the separation of said tissues without the need to make large incisions or injuries to said tissues. Thanks to the space that forms inside the joint under the plate, the interior visibility of the joint is increased. Therefore, the available operatory field is increased, and the surgeon is able to carry out the arthroscopy without the need to make extensive incisions or excessive displacements of the capsule. In short, using the method as per the invention, the capsule of the joint is far less damaged after arthroscopy compared with conventional techniques based on capsulotomies or capsulectomies. This is due to the fact that the need for large incisions is removed along with the subsequent healing of these incisions or injuries, as in the case of said conventional techniques. Therefore, arthroscopic intervention is simplified. Furthermore, thanks to the conservation of the capsule and the tissues adjacent to the joint, post-operative complications are minimized, and thus recovery following arthroscopy is faster and less painful for the patient.

All of the advantages described are applicable to the arthroscopic technique in general. In addition, the application of the method as per the invention is particularly beneficial for arthroscopy applied to those joints in anatomic areas of difficult access. In the particular case of the hip joint, the method as per the invention enables arthroscopy to be performed with more guarantees in terms of maintaining the kinematic functions and stability of the hip, due to all of the aforementioned advantages.

In an optional embodiment of the method as per the invention, the device has a second traction element to facilitate the removal of the device from the joint upon completion of the arthroscopy.

BRIEF DESCRIPTION OF THE FIGURES

The details of the invention can be observed in the accompanying figures, which do not intend to limit the scope of the invention:

FIG. 7 shows a detailed enlarged view of the device of FIG. 2, allowing to observe the second traction element used to remove the device from the joint.

DETAILED DESCRIPTION OF THE INVENTION

Figure 1:
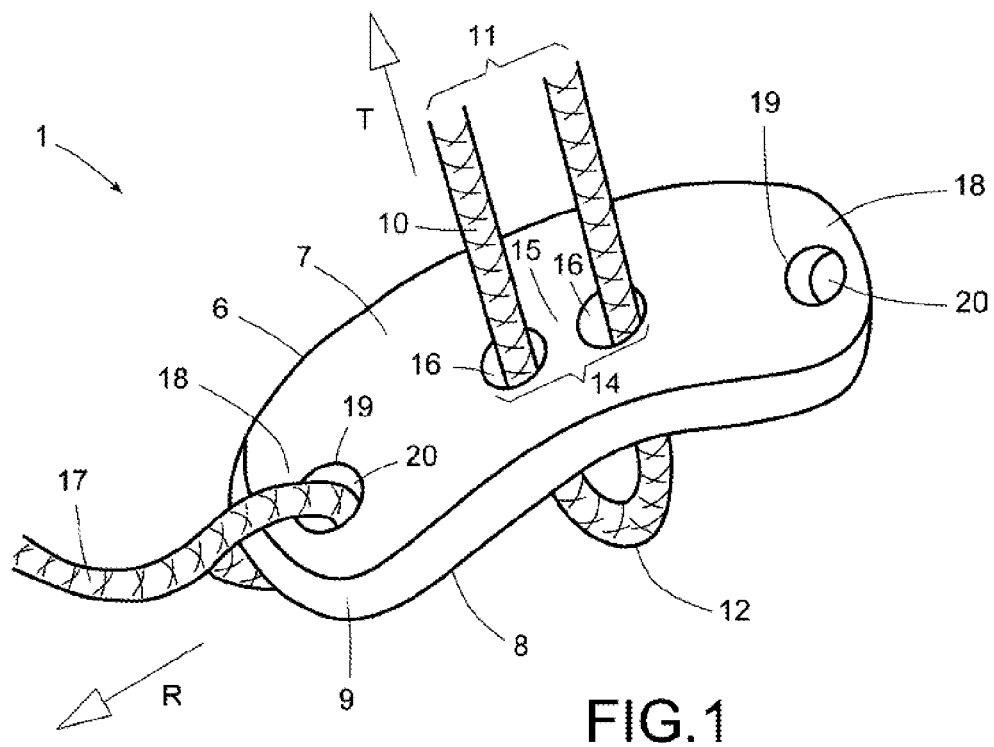
FIG. 1 shows a perspective view of an embodiment of the device in accordance with the invention.
Figure 2:
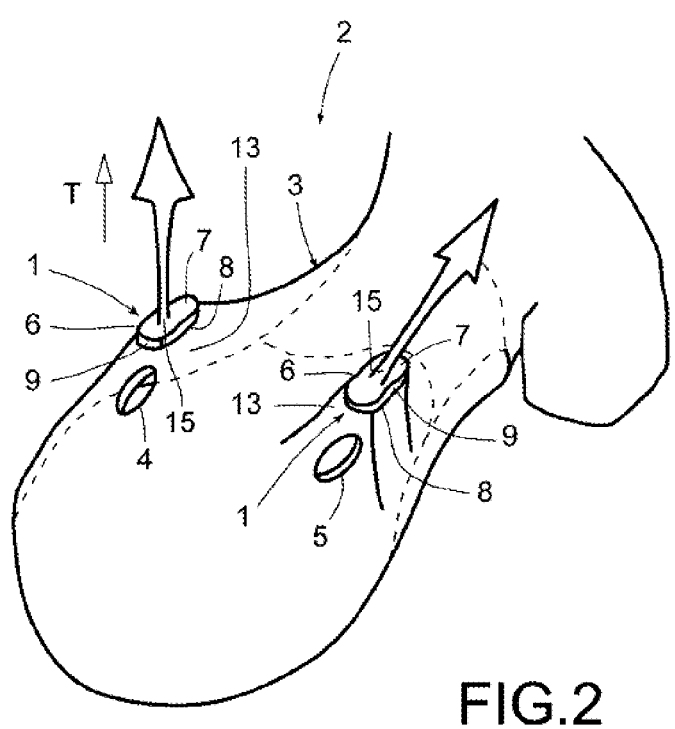
FIG. 2 shows a schematic illustration of the device of FIG. 1 being used for carrying out an exemplary method according to the invention in a hip joint.

The invention relates to a surgical method for the diagnosis or treatment of a patient's joint, wherein the joint is at least partially surrounded by a capsule. The invention also relates to a device for implementing this method, whereby FIG. 1 shows an exemplary embodiment of the device (1). The device (1) is suitable for surgical use and is intended to be inserted inside the patient's joint (2), the device thus being valid for arthroscopic use. It is understood that the device (1) is suitable for surgical use in the sense that the device (1) has been designed to come into contact with the patient's tissues and organic fluids; also, appropriate disinfection or sterilization of the device (1) must be possible following arthroscopic surgery, or the device (1) should be disposable after use. FIG. 2 outlines the position of the device (1) of FIG. 1 inside a joint (2) to carry out an embodiment of the method as per the invention. More specifically, FIG. 2 schematically illustrates the positioning of two devices (1) as per the invention inside a coxofemoral joint, also known as a hip joint. As can also be observed in FIG. 2, the joint (2) is partially surrounded by a capsule (3).

Figure 3:
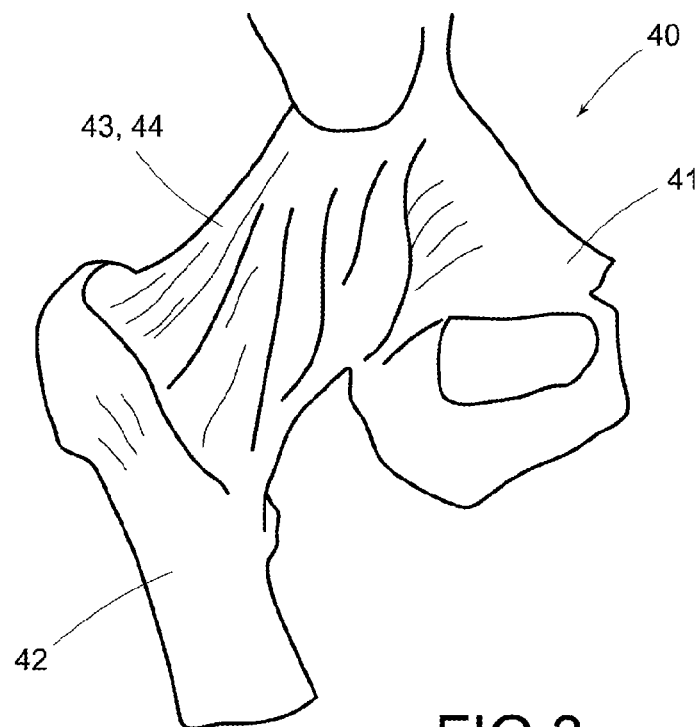
FIG. 3 shows an external view of the anatomy of a hip joint, known in the prior art.
Figure 4:
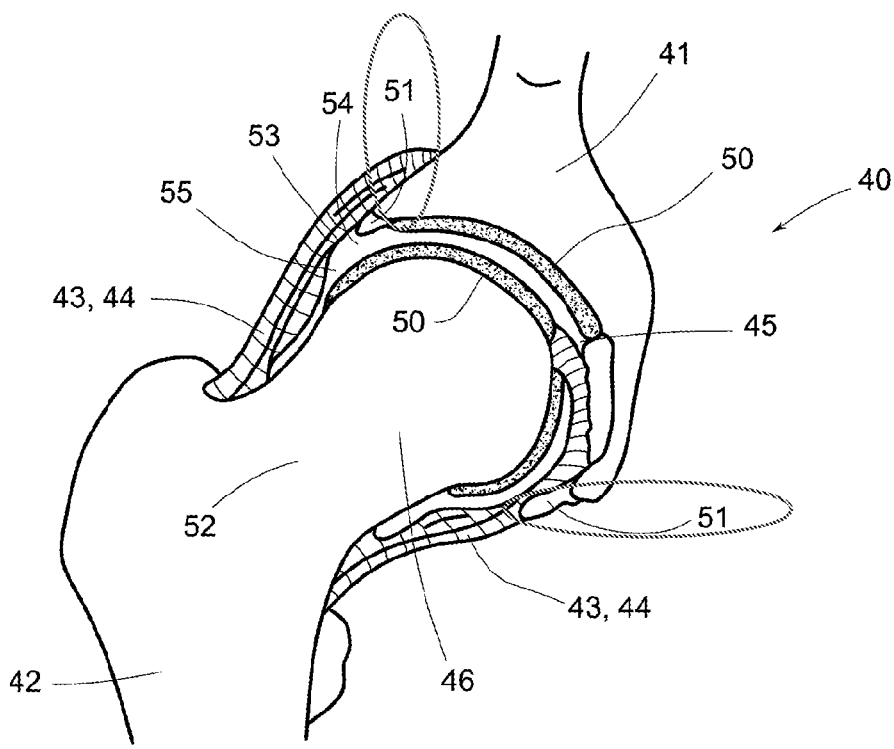
FIG. 4 shows a sectional view of the hip joint, in which some of the internal structures of its anatomy are depicted schematically.
Figure 5:
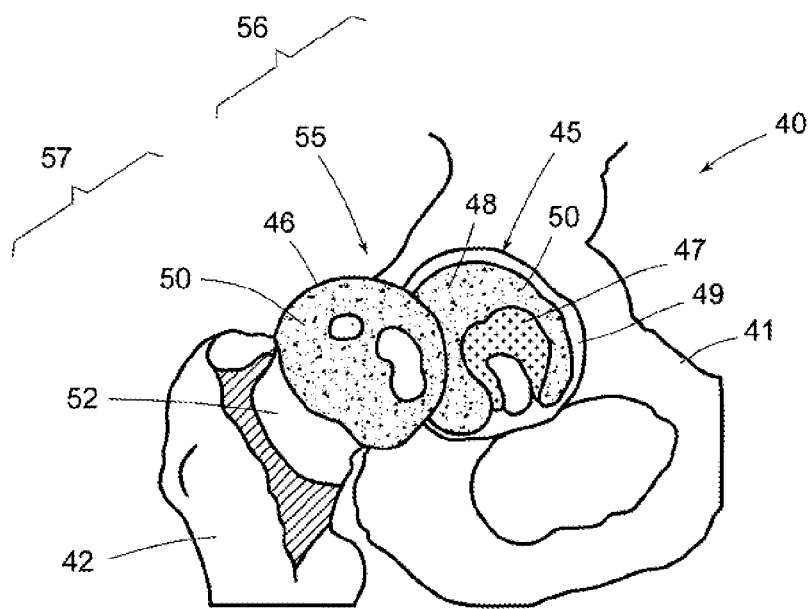
FIG. 5 presents a view of the hip joint in which the bones that make up the joint are shown separately in order to show some of the internal structures of the hip joint in more detail.

The anatomy of the hip joint, known in the prior art, is reviewed hereafter as a prior step to explaining the uniqueness and advantages of the method as per the invention, which will be explained afterwards in detail. FIG. 3 shows an external view of the anatomy of a hip joint (40). FIG. 4 shows a sectional view of the hip joint (40) in which some of the internal structures of its anatomy are outlined. As can be observed in FIGS. 3 and 4, the hip joint (40) joins the coxal bone (41) to the femur (42), hence enabling the connection between the trunk and the lower limbs of the human body and helping to support body weight. In the hip joint (40), as in other movable synovial or diarthrosis joints, the bones remain together as a result of the action of the articular capsule (43) and the complementary work of some associated ligaments (44). The tissues that make up the articular capsule (43) and the ligaments (44) intertwine forming a single functional unit positioned around the hip joint (40) as can be observed in FIGS. 3 and 4. On the other hand, in any movable joint, two articular surfaces are involved in the movement of the movable joint, a relative movement taking place between said surfaces. At the hip joint (40) these articular surfaces are spherical or almost spherical, whereby one articular surface is concave and the other articular surface is convex and allows multi-axial movements or movements in multiple directions. FIG. 5 shows a view of a hip joint (40) when the two bones that make up this joint, the coxal bone (41) and the femur (42), are separated or unlocked to leave the articular surfaces open. As can be observed in FIG. 5, the two articular surfaces that make up the hip joint (40) are: the cotyloid cavity or acetabulum (45), located on the external side of the coxal bone (41), which is a round and deep cavity that is concave in shape; and the femur (46) head, located on the upper end of the femur, which is smooth, spherical and convex in shape. The femur head (46) fits into the acetabulum (45) forming the hip joint (40). This spherical movable joint allows a wide variety of inflection, extension, adduction and rotation movements. The acetabulum (45) has two parts: a central non-articular area (47) called the backdrop of the cotyloid cavity and a peripheral area (48) in the shape of a half moon. The acetabulum (45) is restricted by the acetabular rim (49) also known as the cotiloyd lip. Both the femur head (46) and the peripheral area (48) of the acetabulum (45) are covered with articular cartilage (50) whereby this articular cartilage (50) prevents the two articular surfaces (45, 46) from coming into direct contact with each other. A fibrocartilaginous ring called the cotiloyd ligament or acetabular labrum (51), which is shown in FIG. 4, is inserted between the acetabulum (45) and the head of the femur (46); the acetabular rim (49) is inserted in the acetabular labrum (51) in order to expand the surface of the acetabulum (45) and allow the head of the femur (46) to fit better in the acetabulum (45). The articular capsule (43) that partially surrounds or wraps around the hip joint (40) is a fibrous and resistant sleeve inserted around the articular surfaces, specifically around the femoral neck (52). Due to its resistance, the articular capsule (43) helps provide strength and stability to the hip joint (40) as it reinforces the union between the coxal bone (41) and the femur (42). In addition, the articular capsule (43) has an internal cover, the synovial membrane (53) shown in FIG. 4, which produces a synovial liquid (54). This synovial liquid (54) facilitates relative displacement between the hip joint bones (40). Ligaments (44) are anatomic structures in the form of a band consisting of elastic and resistant fibers. As already mentioned, these ligaments (44) intertwine with the capsular tissue and increase the stability of the hip joint (40). Furthermore, the ligaments (44) allow and facilitate the movement of the hip joint (40) in natural anatomic directions, whilst restricting anatomically abnormal movements or those with excessive amplitude.

The application of the method as per the invention in a hip joint, as shown in FIG. 2, comprises a series of initial steps which are common to other known arthroscopic techniques. In the first place, the patient is normally laid on the operating table to carry out traction on the lower limbs or leg under general anesthetic. This traction of the lower limbs aims to separate the femur (42) towards the exterior of the acetabulum (45) as shown in FIG. 5. In this way, a cavity, inner space or intra-articular space (55) of the hip joint (40) is opened. An initial portal is made, in other words a small incision or access portal, called an anterolateral portal. A guiding needle is inserted through this first portal. This first portal is carried out along a path that is considered to be safe, in which there are no anatomic structures that may be damaged. However, as the specific characteristics of each hip may vary, the first portal may be made with the help of X-rays. The use of X-rays provides somewhat limited, but sufficient, initial visibility enabling for instance the silhouette of the acetabular labrum (51) to be recognized and avoiding its involuntary damage on inserting the guiding needle. The arthroscopic camera is inserted in the intra-articular space (55) via the guiding needle and the area between the acetabular labrum (51) and the head of the femur (46) is identified via direct visualization. A second access portal is then made, known as the anterodistal portal. The necessary instruments are inserted through this second portal with the help of a guiding needle. Normally, for most arthroscopic procedures in the hip, two portals suffice. Furthermore, once both portals have been made, their functions may be interchanged; i.e., the two portals may be used indifferently to insert the cameras and the operating instruments in the intra-articular space (55).

After creating the two portals, conventional arthroscopic techniques comprise a step of making capsulotomies or capsulectomies to expand the opening of the articular capsule (43) and increase the mobility of the operating instruments in the reduced intra-articular space (55) available after the traction of the lower limb. The complex anatomy of the hip joint (40) and the importance of the functions of the articular capsule (43) have already been explained. These characteristics of the hip joint (40) show the importance of keeping the articular capsule (43) as intact as possible during the arthroscopy and the need for considerable knowledge and skill by the surgeon to perform the appropriate capsulotomies or capsulectomies for each specific ailment.

On the other hand, during a hip arthroscopy, two parts or work phases can be identified in different articular compartments (outlined in FIG. 5) separated by the acetabular labrum (51) (not shown in FIG. 5): a central compartment (56) which comprises the acetabulum (45), the central part of the head of the femur (46) and the central part of the acetabular labrum (51); and a peripheral compartment (57) which comprises the femoral neck (52), the most lateral part of the head of the femur (46) and the articular capsule (43) (not shown in FIG. 5). Regardless of the pathology, in most hip arthroscopies, systematic and full inspection of the entire intra-articular space (55) and of all the anatomic structures of the joint is important. The central compartment (56) is normally inspected first, followed by the peripheral compartment (57). In order to work in the peripheral compartment (57), the traction in the lower limb is normally removed and the lower limb is moved into various inflection, rotation or adduction positions to facilitate access to different parts of the peripheral compartment (57). Finally, in order to work in the peripheral compartment (57), conventional arthroscopies may require extending a previous capsulotomy, adding to the aforementioned disadvantages.

The method as per the invention proposes a set of steps which are described hereafter. A first step consists in being provided with at least one device (1) which comprises a plate (6), as can be observed in FIG. 1. The plate (6) is fitted with a first external surface (7) and an opposing second external surface (8). The plate (6) is also fitted with a contour (9) between both external surfaces (7, 8), where this contour (9) is devoid of sharp edges. The device (1) also includes a flexible traction element (10) designed to protrude from the first external surface (7) of the plate (6) forming a variable angle with the first external surface (7). The fact that the angle is variable enables the orientation of the traction element (10) with respect to the external surface (7) of the plate (6) to be adapted or modified.

Figure 6:
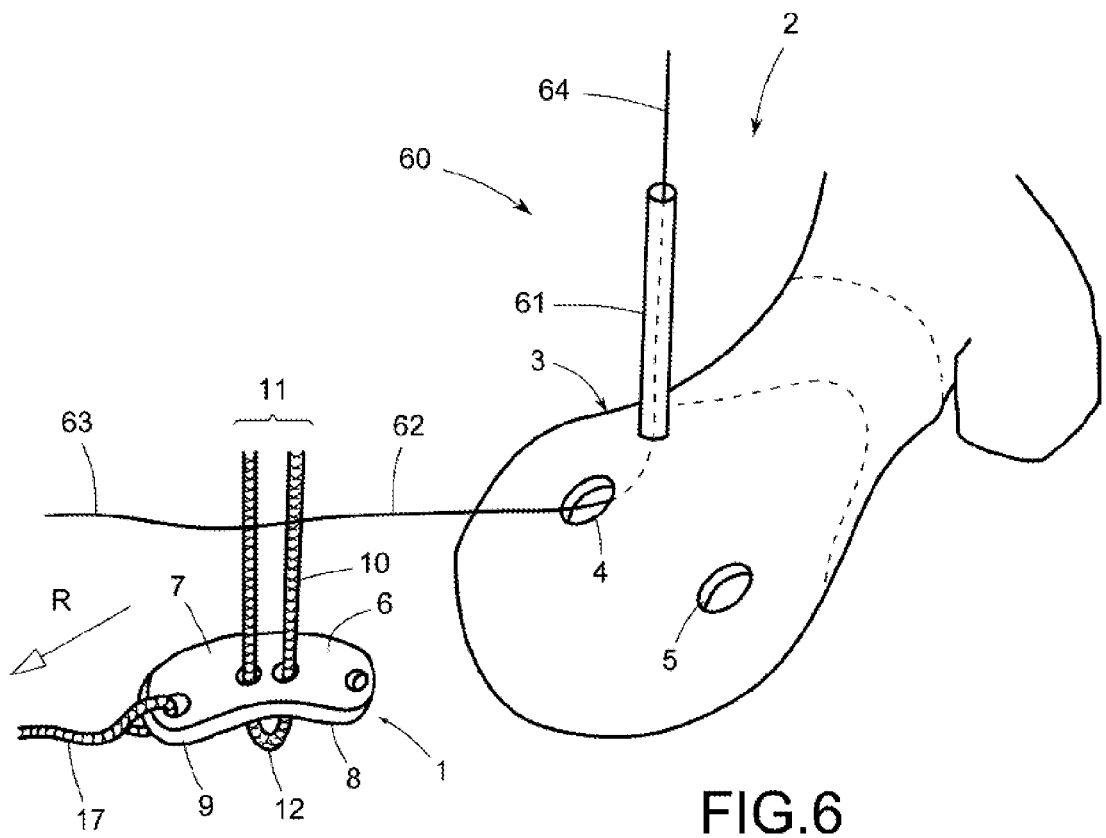
FIG. 6 shows the use of a guiding system to insert the device of FIG. 1 inside the joint of FIG. 2.

The method according to the invention further comprises a second step of inserting the device (1) inside the joint (2), passing through the capsule (3) and ensuring that the traction element (10) protrudes externally and is accessible from outside the patient's body. The device (1) is inserted inside the joint (2) using a guiding system (60) which extends from outside the patient's body to inside the joint (2). FIG. 2 shows two devices (1) which have already been inserted inside the joint (2) and FIG. 6 shows an example of the guiding system (60). FIGS. 2 and 6 show a first access portal (4) and a second access portal (5). The guiding system (60) of FIG. 6 consists of a hollow needle (61) and an auxiliary device, for example, a thread recovery filament (62). The insertion and positioning of the device (1) inside the joint (2), using the guiding system (60) shown in FIG. 6, is performed as described hereafter. First of all, an area of the capsule (3) around the part requiring better visibility is selected and then the capsule (3) is crossed using the hollow needle (61). Entry of the hollow needle (61) in the chosen area of the capsule (3) is observed on the monitor connected to the arthroscopic camera. Using the hollow needle (61), the thread recovery filament (62) is inserted at a first end (63); this first end (63) is removed from the patient's body via one of the portals (4, 5) (in FIG. 6 the first portal (4) has been used). Thus, the thread recovery filament (62) is positioned so that both of its ends (63, 64) are accessible from outside the patient's body. The first end (63) of the thread recovery filament (62) is temporarily connected to the traction element (10) of the device (1). In the device (1) shown in FIGS. 1, 2 and 6, the traction element (10) is specifically a high-resistance thread that can be easily tied or knotted to the first end (63) of the thread recovery filament (62). Thus, as shown in FIG. 6, the traction element (10) is connected to the thread recovery filament (62) by an external end (11) of the traction element (10). By pulling the second end (64) of the thread recovery filament (62), the thread recovery filament (62) is removed or recovered towards the exterior whilst pulling the traction element (10). On pulling, the external end (11) of the traction element (10) is inserted inside the joint (2) and then removed from the joint (2) until this external end (11) protrudes and is externally accessible. FIG. 7 shows an enlarged detailed view of the device (1) of FIG. 2, in which the more detailed positioning of the device (1) as per the invention can be observed inside the joint (2). As can be observed in FIG. 7, the whole device (1) is inserted inside the joint (2) via the previously described pulling movement. However, the plate (6) of the device (1) is not able to cross the capsule (3) due to its dimensions, whereby it remains inside the joint (2).

The guiding system may be variable, and is just as valid to carry out the method as per the invention, provided that the traction element (10) protrudes and remains accessible externally.

Once the device (1) has been inserted inside the joint (2), enabling the traction element (10) to protrude externally, the method as per the invention comprises a step of pulling the traction element (10), causing this traction element (10) to position itself in a non-tangent position to the first external surface (7) of the plate (6) and causing this external surface (7) to come into contact with the internal wall of the capsule (3) Once the plate (6) has come into contact with the capsule (3) wall, the next step of the method as per the invention consists in continuing to pull the traction element (10) in a non-tangent T direction to the first external surface (7). In this way, the plate (6) pushes the internal wall of the capsule (3) causing the deformation of the capsule (3), as can be observed in FIGS. 2 and 7. As a result of this deformation, a viewing window or space (13) is delimited under the plate (6) and inside the joint (2). The traction that causes the aforementioned deformation is an intra-articular traction, i.e., it is exercised from inside the joint (2). Thus, the invention offers a method that allows the tissues to be separated without the need to use capsulotomies or capsulectomies. Furthermore, thanks to the space (13) that is delimited under the plate (6), better exposure of the available operating field is obtained for the surgeon because visibility inside the joint (2) is increased. This increased visibility facilitates the surgeon's work in the central compartment (56) of a hip joint (40) and is particularly advantageous when working in the peripheral compartment (57). The reason is that visibility is further limited in this peripheral compartment (57) due to the anatomic characteristics previously explained in this document. As can be observed in FIG. 2, it is possible to use more than one device (1) if greater visibility is required in various areas of the capsule (3).

The embodiment of the device (1) shown in FIGS. 1, 2 and 7 enables the method as per the invention to be carried out. The device (1) is suitable for arthroscopic use and is intended to be inserted inside a joint (2), such as, for example, a hip joint like the one outlined in FIG. 2. The device (1) is inserted inside the joint (2) via the use of arthroscopic portals (4, 5) which are commonly used in arthroscopies. As can be observed in FIG. 1, the device (1) is unique as it consists of a plate (6) with a first external surface (7) and a second opposing external surface (8). The plate (6) is also fitted with a contour (9) between both external surfaces (7, 8). The contour (9) is devoid of sharp edges to avoid damage to the capsule (3) tissues or in other adjacent tissues with which the device (1) comes into contact. Furthermore, the device (1) consists of a flexible traction element (10) designed to protrude from the first external surface (7) of the plate (6) forming a variable angle with this first external surface (7). The flexibility of the traction element (10) ensures that the device (1) protrudes externally and is accessible from outside the patient's body, once the device (1) has been inserted inside the joint (2). As can be observed in detail in FIG. 7, an external end (11) of the traction element (10) protrudes externally and the internal end (12) of the traction element remains inside the joint (2). As the traction element (10) protrudes externally, traction of the plate (6) is achieved as follows: on pulling the external end (11) of the traction element (10), the traction element (10) is capable of positioning itself in a non-tangent position to the first external surface (7) so that the first external surface (7) of the plate (6) comes into contact with the internal wall of the capsule (3). This positioning is possible thanks to the orientation or angle between this traction element (10) and the first external surface (7) of the plate is variable or adaptable. On coming into contact with the internal wall of the capsule (3), the plate (6) adopts a transversal position with respect to a T direction and places its largest area against the internal wall of the capsule (3) so that the plate (6) is unable to pass through this internal wall due to its dimensions. In the previous situation, if the traction or pulling action of the external end (11) of the traction element (10) is maintained, the plate (6) pushes the internal wall of the capsule (3) and this pushing causes the deformation of the capsule (3). FIG. 2 outlines how the capsule tissues (3) are raised in the T direction. As a result of this deformation, a space (13) under the plate (6) and inside the joint (2) is delimited. In FIGS. 2 and 7, the space (13) is triangular in shape, similarly to a tent. In this way, the device (1) enables intra-articular traction (traction from inside the joint (2)) of the capsule tissues (3) to be performed without the need for making large incisions like in conventional arthroscopic techniques. Thanks to the space (13) delimited under the plate (6), visibility inside the joint (2) is increased.

The size of the plate (6) may vary depending on the joint to be treated. In the device (1) shown in the figures, the plate is metallic and the approximate dimensions of this plate (6) are preferably one centimeter long, half a centimeter wide and one millimeter deep, to adapt to the specific size of a hip joint. Devices (1) in which the plate (6) is made out of another material, such as, for example peek or another resistant plastic, or other materials with sufficient resistance to allow effective and risk-free traction of the device (1) are also contemplated. Traction is considered to be effective and risk-free if the material is suitable for surgical use and allows intra-articular traction as described.

In spite of the fact that the capsule (3) of the joint (2) presents certain elasticity that favors the aforementioned deformation, the first external surface (7) of the plate (6) is optionally convex to adapt optimally to the capsule (3) and facilitate this deformation. Thanks to the elasticity of the capsule (3), a slight degree of convexity of the first external surface (7) is required to obtain better adaptation between the first external surface (7) and the capsule (3) and to favor the deformation of the capsule (3).

As shown in FIG. 1, the plate (6) of the device (1) optionally comprises a connection element (14) which enables the traction element (10) to be removably connected to the plate (6). The traction element (10) is connected to this connection element (14) at the lower end (12).

The method as per the invention optionally comprises the additional step of connecting the traction element (10) to the connection element (14). The connection between the elements (10, 14) is carried out prior to inserting the traction element (10) inside the joint (2). This additional step particularly recommended when the traction element (10) is removable.

The connection element (14) is optionally arranged at a central area (15) of the plate (6), and the plate (6) is substantially symmetrical with respect to a transversal axis arranged in the central area (15). The central location of the connection element (14) ensures that the pulling of the traction element (10) in the T direction makes the plate (6) adopt a transversal position with respect to this T direction, maximizing the surface area that contacts the internal wall of the capsule (3). Therefore, a more balanced deformation of the capsule (3) is obtained.

The connection element (14) optionally comprises at least one hole (16) which is devoid of cutting edges to prevent deterioration of the traction element (10). In FIG. 1, the connection element (14) has two holes (16) through which the traction element (10) may loosely pass. Therefore, the connection between the traction element (10) and the plate (6) is performed quickly and easily.

Optionally, the traction element (10) is a high-resistance thread such as that shown in FIG. 7. As can be observed in this figure, the high-resistance thread passes through both holes (16) and is accessible from outside the joint (2). The ends of the high-resistance thread form the external end (11) of the traction element (10). The intermediary part of the high-resistance thread, i.e. the part that is closest to the holes (16), forms the internal end (12). The choice of high-resistance thread as the traction element (10) is advantageous due to its resistance.

Other types of traction elements and other types of connection element are also contemplated. These elements will be just as valid for the implementation of the method as per the invention provided that the connection between the traction element (10) and the plate (6) has sufficient resistance to allow effective and risk-free traction of the device (1).

To help remove the device (1) from the joint (2) upon completion of the arthroscopy, the device (1) in the method as per the invention optionally comprises a second traction element (17). FIGS. 6 and 7 show this second traction element (17), which is flexible and is designed to protrude from a lateral area (18) of the plate (6) and allow the traction of the plate (6) in a longitudinal R direction to the plate (6). If this second traction element (17) is included, the method as per the invention comprises the following additional steps: allowing the second traction element (17) to protrude externally and remain accessible from outside the patient's body; pulling the second traction element (17), causing this second traction element (17) to be positioned longitudinally to the plate (6); and continuing to pull the second traction element (17) in the R direction, causing removal of the device (1) from the joint (2). In the figures, the second traction element (17) is accessible from the exterior via one of the portals (4, 5) once the device (1) has been inserted inside the joint (2) via the guiding system (60). In this process, the second traction element (17) is a high-resistance thread, as the traction element (10), due to the aforementioned advantages. On pulling the second traction element (17) the plate (6) adopts a longitudinal position in the R direction so as to offer as little resistance as possible and facilitate the removal of the device (1) from the joint (2). In this way, the removal of the device (1) from the joint (2) does not damage the tissues with which the device (1) comes into contact on being removed from inside the patient.

The plate (6) optionally comprises an additional connection element (19) which enables the second traction element (17) to be removably connected to the plate (6). This additional connection element (19) is located in a lateral area (18) of the plate (6), whereby this lateral area (18) is close to the contour (9) of the plate (6). The lateral location of the additional connection element (19) favors the positioning of the plate (6) in the R longitudinal direction and, therefore, the removal of the device (1) from the joint (2).

The additional connection element (19) optionally comprises at least one hole (20) that is devoid of cutting edges to prevent the deterioration of the second traction element (17). This hole (20) enables the connection between the second traction element (17) and the plate (6) to be performed quickly and easily. In the Figures, the device (1) has two holes (20), located on two opposing sides of the lateral area (18) of the plate (6), which can be used for the removal of the device (1).

The invention also contemplates devices with other second traction elements or other additional connection elements, that can adopt different shapes, provided that they facilitate the removal of the device (1) from the joint (2).

The invention also contemplates devices (1) in which the plate (6), the traction element (10) and the second traction element (17) represent a set or kit that can be disposed of after the arthroscopy.

The plate (6) is optionally made out of a radio-transparent material and consists of an X-ray marker. These characteristics allow for the recovery of the device (1) via X-rays, which may be particularly beneficial in certain circumstances: for example, in the event of a disconnection between the traction element (10) and the plate (6) as a result, for example, of a manufacturing fault in the device (1) or for other reasons.

The invention claimed is:

1. A method for the diagnosis or treatment of a joint of a patient, wherein said joint is at least partially surrounded by a capsule, wherein said method comprises the steps of:
   being provided with at least one device comprising a plate, in which the plate has a first external surface and a second external surface opposite to each other, a contour between both external surfaces, wherein said contour is devoid of cutting edges, and a traction element that protrudes from the first external surface of the plate forming a variable angle with said first external surface;
   inserting the device inside the joint and passing through the capsule, ensuring that the traction element protrudes externally and remains accessible from outside the patient's body;
   pulling the traction element, causing said traction element to become placed in a non-tangent position to the first external surface of the plate and causing said external surface to come into contact with an internal wall of the capsule;
   continuing to pull the traction element in a non-tangent direction T to the first external surface, causing the plate to push the internal wall of the capsule and cause a deformation of the capsule, there becoming delimited a space under the plate and inside the joint as a result of said deformation.

2. The method, according to claim 1, further comprising an additional step of connecting the traction element to a central area of the plate prior to inserting the device inside the joint.

3. The method, according to claim 2, wherein, in said additional step, the traction element passes through at least one hole in the central area, wherein said hole is devoid of cutting edges.

4. The method, according to claim 3, wherein the traction element is a high-resistance thread.

5. The method, according to claim 1, wherein the device comprises a second flexible traction element designed to protrude from a lateral area of the plate and to allow traction of the plate in a longitudinal direction R to the plate, and wherein the method further comprises the steps of:
   allowing the second traction element to protrude externally and remain accessible from outside the patient's body;
   pulling the second traction element, causing this second traction element to be placed in a longitudinal position to the plate;
   continuing to pull the second traction element in the R direction and causing the removal of the device from the joint.

6. The method, according to claim 5, further comprising a prior step of securing the second traction element to the lateral area of the plate.

7. The method, according to claim 6, wherein, in said prior step, the second traction element is secured to a hole devoid of cutting edges.

* * * * *